United States Patent
Reynolds et al.

(10) Patent No.: US 6,222,041 B1
(45) Date of Patent: Apr. 24, 2001

(54) METHOD FOR THE PRODUCTION OF 2-MERCAPTOBENZOTHIAZOLE

(75) Inventors: Michael P. Reynolds; Russell E. Malz, Jr., both of Naugatuck, CT (US)

(73) Assignee: Uniroyal Chemical Company, Inc., Middlebury, CT (US)

( * ) Notice: Subject to any disclaimer, the term of this patent is extended or adjusted under 35 U.S.C. 154(b) by 0 days.

(21) Appl. No.: 09/512,098

(22) Filed: Feb. 24, 2000

(51) Int. Cl.$^7$ .................................................. C07D 277/72
(52) U.S. Cl. .............................................................. 548/176
(58) Field of Search ............................................. 548/176

(56) References Cited

U.S. PATENT DOCUMENTS

| | | | |
|---|---|---|---|
| 1,631,871 | 6/1927 | Kelly ..................................... | 548/176 |
| 1,712,968 | 5/1929 | Roberts et al. ....................... | 548/175 |
| 2,001,587 | 5/1935 | Semon et al. ......................... | 260/44 |
| 3,818,025 | 6/1974 | Sugahara et al. .................... | 260/306 |
| 4,316,031 | 2/1982 | Bergfeld et al. ..................... | 546/175 |

FOREIGN PATENT DOCUMENTS 2 018 774   4/1978   (GB) .

OTHER PUBLICATIONS

Ivanova et al., Journal of Applied Chemistry of the USSR, vol. 30, No. 3, (Mar., 1957), pp. 473–479.

*Primary Examiner*—Laura L. Stockton
(74) *Attorney, Agent, or Firm*—Raymond D. Thompson; Paul Grandinetti

(57) ABSTRACT

An improved process for the preparation of 2-mercaptobenzothiazole by reacting aniline, nitrobenzene, and carbon disulfide is disclosed wherein the improvement comprises employing a reaction temperature profile comprising the steps of:

(A) heating the reactants to at least one temperature less than or equal to about 150° C.;

(B) then heating the reactants to a temperature in the range of from about 150° C. to about 170° C.; and (C) then heating the reactants to a temperature in the range of from about 220° C. to about 275° C.

9 Claims, No Drawings

US 6,222,041 B1

METHOD FOR THE PRODUCTION OF 2-MERCAPTOBENZOTHIAZOLE

BACKGROUND OF THE INVENTION

1. Field of the Invention

This invention relates to an improved method for the production of 2-mercaptobenzothiazole.

More particularly, the invention relates to an improvement in a method for the production of 2-mercaptobenzothiazole from aniline, nitrobenzene, and carbon disulfide.

2. Description of Related Art

It is well known that 2-mercaptobenzothiazole is useful as a vulcanization accelerator for natural and synthetic rubbers and as a starting material in the synthesis of other thiazole compounds that are also useful as vulcanization accelerators.

One commercial means for the synthesis of 2-mercaptobenzothiazole involves the reaction of aniline, carbon disulfide, and sulfur. The overall chemistry of this reaction can be represented by the following equation.

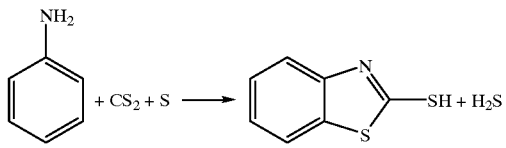

Although this chemistry is straightforward, it is an oversimplification of the actual chemistry, which occurs through a variety of intermediates.

U.S. Pat. No. 1,712,968 discloses a process wherein an aromatic thiourea, e.g., thiocarbanilide, is reacted with carbon disulfide and sulfur according to the equation:

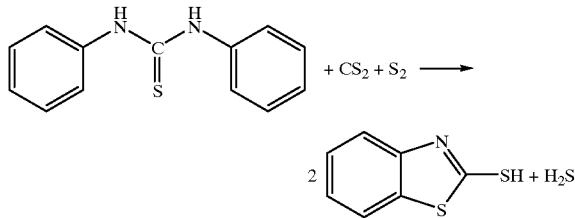

The reaction is run in an autoclave, which is slowly heated so that the temperature of the contents of the autoclave increases at a rate of approximately one degree per minute. This rate of heating is continued until the temperature reaches 225° C., whereupon the heat is moderated so that the temperature rise is about one degree every two minutes, and this rate is continued until the contents of the autoclave has reached a temperature of about 275° C. The time required for attaining the temperature mentioned under the conditions specified is approximately from five to six hours.

U.S. Pat. No. 2,001,587 discloses a method for preparing mercapto arylene thiazoles consisting of reacting a mixture of carbon disulfide, and arylamine and an organic oxidizing agent, such as an aromatic nitro compound, according to the equation:

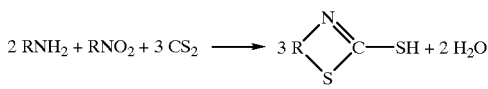

wherein R represents an aromatic nucleus. The reactants are heated in an autoclave at 220° C. for six hours.

U.S. Pat. No. 3,818,025 discloses a process for the production of 2-mercaptobenzothiazole by the reaction of aniline, carbon disulfide and sulfur at a high temperature under elevated pressure, characterized in that the reaction is carried out first at 250° to 300° C. and then at 200° to 240° C.

U.S. Pat. No. 4,316,031 discloses a process for the preparation of 2-mercaptobenzothiazole comprising heating a reaction mixture comprising nitrosobenzene, hydrogen sulfide and carbon disulfide in a molar ratio of about 1:1.5 to 4:1 to 3, respectively, to a temperature from about 200 to about 300° C., for a time sufficient to convert at least a portion of the reactants into 2-mercaptobenzothiazole. In an alternative process, there is first reacted nitrosobenzene with hydrogen sulfide in a molar ratio of about 1:1.5 to 4, at a temperature from about 20 to about 100° C. for a period of time sufficient to substantially reduce the nitrosobenzene, and subsequently reacting the resulting product mixture with from about 1 to about 3 mole equivalents of carbon disulfide per mole of originally charged nitrosobenzene, at a temperature from about 200° C. to about 300° C.

U.K. Patent Application GB 2 018 774 A discloses a process for the preparation of 2-mercaptobenzothiazole which comprises reacting nitrobenzene or nitrosobenzene, hydrogen sulphide and carbon disulphide, the molar ratio of nitrobenzene or nitrosobenzene:hydrogen sulphide being from 1:3 to 1:6 or from 1:1.5 to 1:4, the molar ratio of nitrobenzene or nitrosobenzene:carbon disulphide being from 1:1 to 1:3 and the final reaction temperature being from 200 to 300° C.

Embodiments are disclosed wherein (a) nitrobenzene and $H_2S$ are reacted in a specified molar ratio under elevated temperature and pressure and the resulting reaction mixture is reacted with $CS_2$ in a specified molar ratio at 200 to 300° C.; (b) nitrosobenzene, $H_2S$ and $CS_2$ are reacted in a specified molar ratio at 200 to 300° C.; and (c) nitrosobenzene and $H_2S$ are reacted in a specified molar ratio at 20 to 100° C. and the resulting reaction mixture is reacted with $CS_2$ in a specified molar ratio at 200 to 300° C.

The disclosures of the foregoing are incorporated herein by reference in their entirety.

SUMMARY OF THE INVENTION

The present invention is directed to an improvement in the process for making 2-mercaptobenzothiazole that is represented by the overall equation:

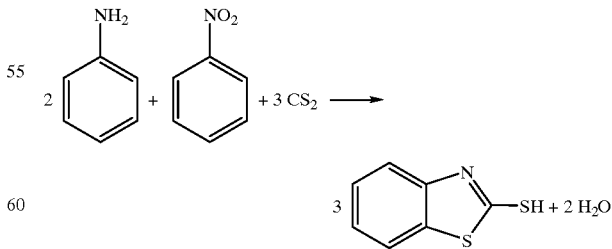

wherein the improvement is directed to the control of the temperatures at the several stages of the reaction.

More particularly, the present invention is directed to an improved process for the preparation of 2-mercaptobenzothiazole by reacting aniline, nitrobenzene, and carbon disulfide wherein the improvement comprises employing a reaction temperature profile comprising the steps of (A) heating the reactants to at least one temperature less than or equal to about 150° C.;
(B) then heating the reactants to a temperature in the range of from about 150° C. to about 170° C.; and
(C) then heating the reactants to a temperature in the range of from about 220° C. to about 275° C.

DESCRIPTION OF THE PREFERRED EMBODIMENTS

As disclosed above, the present invention is directed to an improved process for the preparation of 2-mercaptobenzothiazole by reacting aniline, nitrobenzene, and carbon disulfide according to the overall equation:

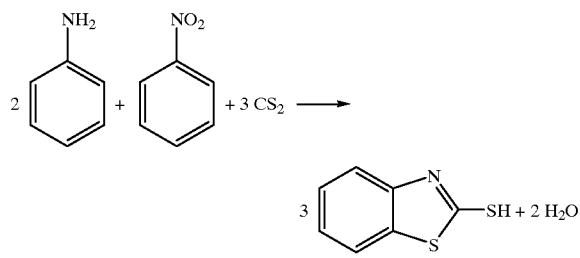

It should be understood that the above is an "overall" reaction equation, which is currently believed to be an integration of at least three individual reactions that may be represented by the following:

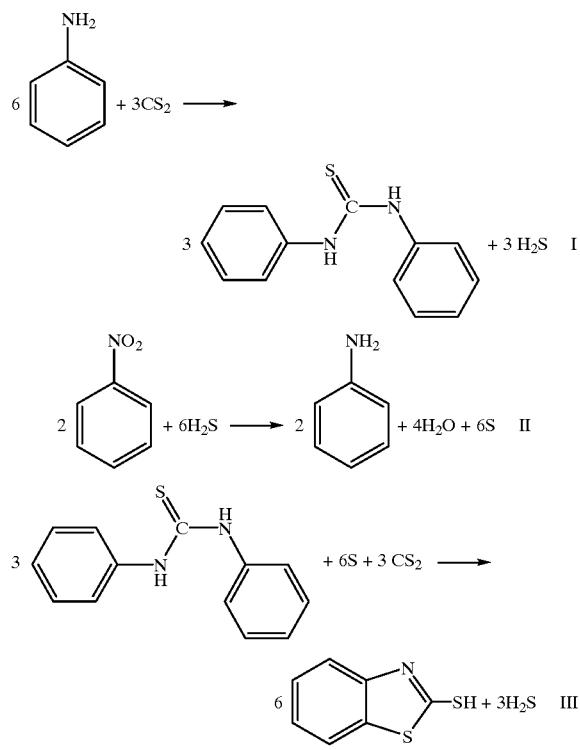

Equation I above represents the formation of thiocarbanilide from aniline and carbon disulfide. Above 160° C., thiocarbanilide decomposes to form aniline and carbon disulfide. See V. A. Ivanov et al., *Zhur. Priklad Khim.* 30:447 (1957) (*Chemical Abstracts* 51:14688 (1957)) Additionally, at 140° C., thiocarbanilide will react with hydrogen sulfide to produce aniline and carbon disulfide. Thus, the formation of the thiocarbanilide in the first stage of the reaction of the present invention requires the balancing of a delicate equilibrium, with the best temperature being at or below 150° C., preferably in a range of from about 140° C. to about 150° C.

Equation II above represents the reduction of nitrobenzene using hydrogen sulfide as the reducing agent. In the absence of catalyst, hydrogen sulfide only reduces nitrobenzene to any significant extent at 150° C. or above, but at temperatures above 170° C., e.g., 200° C., viscous polymers are formed. See U.K. Patent Application GB 2 018 774 A. Thus, the temperature must be kept at or above about 150° C., but no higher than about 170° C. during the second stage of the reaction of the present invention.

Equation III above represents the third stage of the reaction of the present invention and comprises the reaction of thiocarbanilide with carbon disulfide and sulfur to form 2-mercaptobenzothiazole and hydrogen sulfide. It is known from U.S. Pat. No. 1,712,968 that this reaction can be carried out at a temperature in the range of from 220° C. to 275° C.

Those skilled in the art will recognize that both the first step of the reaction and the second can be run at 150° C. If this is done, the first two reactions are, in substance, run at the same time and the process then has a two-step profile, rather than a three-step profile. It should also be noted that the only by-product of the overall reaction of the present invention is water, the hydrogen sulfide that is formed being consumed in the reaction to produce the 2-mercaptobenzothiazole.

The advantages and the important features of the present invention will be more apparent from the following examples.

EXAMPLES 1 AND 2

Comparative Examples

Examples 1 and 2 were each run under 100 psig of nitrogen in a one liter stainless steel autoclave into which 1.5 moles of aniline (139.5 g), 0.6 mole of nitrobenzene (73.8 g), and 1.8 moles of carbon disulfide (136.8 g) had been charged. Example 1 was run for three hours at 220° C. and Example 2 was run for one hour at 1700 C and one hour at 250° C. The results are shown in Table 1;

TABLE 1

| | Wt % | % MBT | Weight Percent Others[1] | | | | | | | |
|---|---|---|---|---|---|---|---|---|---|---|
| Example | MBT | Yield | NB | Aniline | BT | TC | 2ATP | 2ABT | $S_2$ | Total |
| 1 | 57.3 | 55 | <0.1 | 17.1 | 2.4 | 0.3 | 0.9 | 9.4 | 2.3 | 89.8 |
| 2 | 49.4 | 47 | <0.1 | 14.0 | 3.2 | 0.2 | 1.8 | 8.6 | 1.8 | 79.1 |

[1]The weight percent for 2ATP may include 2-aminophenyldisulfide since these two components elute at the same time during HPLC analysis.
MBT = 2 mercaptobenzothiazole
NB = nitrobenzene
BT = benzothiazole
TC = thiocarbanilide
2ATP = 2-aminothiophenol
2ABT = 2-anilinobenzothiazole Example 1 demonstrates that only low yields could be achieved by the single temperature method described in U.S. Pat. No. 2,001,587.

EXAMPLES 3–5

Examples 3, 4, and 5 were each run under 100 psig of nitrogen in a one liter stainless steel autoclave into which 1.2 moles of aniline (111.6 g), 0.6 mole of nitrobenzene (73.8 g), and 2.7 moles of carbon disulfide (205.2 g, a 50% molar excess) had been charged. Example 3 was run for one hour at 130° C., one hour at 145° C., one hour at 160° C., and then three hours at 250° C. Example 4 was run for one hour at 130° C., one hour at 160° C., and then two hours at 250° C. Example 5 was run for one hour at 1300 C, one hour at 145° C., one hour at 160° C., and then two hours at 250° C. The results are shown in Table 2

TABLE 2

| | Wt % | % MBT | Weight Percent Others | | | | | | | |
|---|---|---|---|---|---|---|---|---|---|---|
| Example | MBT | Yield | NB | Aniline | BT | TC | 2ATP | 2ABT | $S_2$ | Total |
| 3 | 81 | 81 | <0.2 | <0.1 | 6.1 | 2.7 | 0.5 | 2.5 | 4.3 | 97.3 |
| 4 | 70 | 70 | <0.2 | 0.4 | 4.3 | 5.3 | 0.5 | 7.5 | 4.9 | 93.2 |
| 5 | 69 | 70 | <0.2 | 0.6 | 4.1 | 5.8 | 0.7 | 9.5 | 5.2 | 94.4 |

Examples 3 through 5 demonstrate the improved results that can be obtained, as compared to those of the above comparative examples, employing the temperature profile of the present invention along with a molar excess of $CS_2$.

EXAMPLE 6

Example 3 was repeated except that the molar excess of carbon disulfide was reduced to 16% (2.1 moles, 159.6 g). The yield of 2-mercaptobenzothiazole was improved over that of the comparative examples, but was lower than that achieved in Example 3. The results are shown in Table 3.

EXAMPLE 7

Comparative Example

Example 6 was repeated except that the reaction was run for one hour at 130° C., one hour at 145° C., and one hour at 160° C. for a total time of three hours. The yield of 2-mercaptobenzothiazole was negligible. The results are shown in Table 3.

TABLE 3

| | Wt % | % MBT | Weight Percent Others | | | | | | | |
|---|---|---|---|---|---|---|---|---|---|---|
| Example | MBT | Yield | NB | Aniline | BT | TC | 2ATP | 2ABT | $S_2$ | Total |
| 6 | 74.5 | 69 | <0.1 | 5.0 | 5.3 | 0.6 | 0.6 | 3.6 | 2.4 | 92.1 |
| 7 | 0.2 | — | 28.3 | 0.05 | 0.4 | 64.6 | <0.1 | 0.2 | 3.6 | 97.5 |

Example 6 demonstrates that reducing the molar excess of carbon disulfide results in a significantly higher percentage of aniline and 2-aminobenzothiazole. The amount of thiocarbanilide is lower owing to the unreacted aniline. It is believed that the yield of MBT using this level of $CS_2$ can be improved by further adjustment of the temperature profile.

Example 7 indicates the intermediates that have been formed at the end of the low temperature profile. This demonstrates that nitrobenzene remains unreacted and could lead to by-product formation if the temperature is increased before its consumption.

EXAMPLES 8–23

Examples 8 through 23 were each run under 150 psig of nitrogen in a one liter stainless steel autoclave. Each Example used 1.2 moles of aniline (111.6 g), 2.1 moles of $CS_2$ (159.6 g), and 0.6 mole of nitrobenzene (73.8 g). The reactants were charged to the autoclave, purged with nitrogen, pressure tested, and reacted for the times specified in Table 4. The by-product $H_2S$ was vented and neutralized into a caustic bath inside a 20 gallon autoclave. The autoclave was unloaded by the operator using a full face mask for additional protection against residual $H_2S$. The weight of the material removed from the autoclave was recorded and is shown in Table 4.

The samples were analyzed for MBT and "Others" by weight percent High Pressure Liquid Chromatography and Gas Chromatography Derivatization. The results permitted the determination of the yield of MBT and examination of by-product formation produced in each Example.

The results can be seen in Table 5. Raw analysis indicated good reproducibility among the Examples. The weight percents and yields of MBT were duplicated with reasonable reproducibility for similar Examples.

The data were examined using linear, quadratic, and cubic regressions using an E-Chip system which generated a statistical experimental design. The data were analyzed using a spread sheet to compare it to the E-Chip analysis, to determine how well the data correlate to the mathematical analysis, and to estimate yields from the spread sheet data regression.

TABLE 4

| Example | Hours @ 150° C. | Hours @ 235° C. | Wt. Collected (gms.) |
|---|---|---|---|
| 8 | 3 | 1 | 288.0 |
| 9 | 2 | 3 | 278.7 |
| 10 | 3 | 3 | 274.8 |
| 11 | 1 | 1 | 288.2 |
| 12 | 3 | 1 | 284.0 |
| 13 | 3 | 2.3 | 275.5 |
| 14 | 2 | 3 | 281.8 |
| 15 | 1 | 2 | 280.6 |
| 16 | 1.7 | 2.3 | 261.4 |
| 17 | 2.3 | 1 | 269.2 |
| 18 | 3 | 3 | 304.5 |
| 19 | 1.7 | 1 | 262.4 |
| 20 | 3 | 1.7 | 273.9 |
| 21 | 1 | 2 | 268.3 |
| 22 | 1 | 3 | 251.8 |
| 23 | 1 | 3 | 275.3 |

TABLE 5

| | Wt % | % MBT | Weight Percent Others | | | | | | | |
|---|---|---|---|---|---|---|---|---|---|---|
| Example | MBT | Yield | NB | Aniline | BT | TC | 2ATP | 2ABT | $S_2$ | Total |
| 8 | 6.5 | 6.2 | <0.2 | 8.3 | <0.2 | 27.4 | 1.1 | 33.7 | 21.8 | 98.5 |
| 9 | 57.4 | 53.2 | <0.2 | 5.7 | 3.1 | 3.6 | 1.0 | 12.2 | 9.7 | 92.4 |
| 10 | 54.7 | 50.0 | <0.5 | 5.1 | 2.5 | 4.2 | 0.4 | 16.4 | 4.6 | 88.9 |
| 11 | 4.5 | 4.3 | <0.5 | 6.3 | 0.1 | 31.3 | 0.4 | 29.9 | 7.1 | 79.6 |
| 12 | 6.0 | 5.8 | <0.5 | 10.2 | 0.2 | 22.8 | 0.6 | 29.9 | 4.9 | 74.6 |
| 13 | 35.4 | 32.4 | <0.5 | 4.8 | 1.5 | 10.7 | 0.7 | 29.1 | 4.0 | 86.2 |
| 14 | 55.0 | 51.6 | <0.5 | 6.2 | 2.4 | 4.8 | 0.6 | 17.2 | 3.3 | 89.5 |
| 15 | 25.6 | 23.9 | <0.5 | 2.8 | 0.9 | 16.4 | 0.5 | 32.2 | 9.8 | 88.7 |
| 16 | 49.1 | 42.7 | <0.5 | 6.6 | 1.7 | 4.6 | 0.6 | 21.3 | 6.7 | 91.1 |
| 17 | 7.0 | 6.3 | <0.5 | 2.2 | 0.2 | 37.1 | 0.3 | 28.6 | 15.2 | 91.1 |
| 18 | 51.2 | 51.9 | <0.5 | 4.0 | 2.0 | 4.9 | 0.3 | 14.5 | 6.1 | 83.5 |
| 19 | 47.2 | 41.2 | <0.5 | 16.3 | 2.2 | 2.9 | 1.2 | 12.8 | 7.0 | 90.1 |
| 20 | 29.4 | 26.8 | <0.5 | 2.6 | 1.1 | 16.2 | 1.7 | 31.7 | 7.3 | 90.5 |
| 21 | 37.4 | 33.4 | <0.5 | 4.0 | 1.6 | 11.0 | 2.2 | 27.8 | 7.6 | 92.1 |
| 22 | 55.7 | 46.7 | <0.5 | 7.5 | 2.4 | 3.2 | 3.0 | 15.8 | 4.8 | 92.9 |
| 23 | 57.6 | 52.6 | <0.5 | 4.3 | 2.2 | 4.6 | 1.5 | 20.5 | 5.7 | 96.9 |

E-Chip analysis using a linear mathematical analysis of the yields of MBT obtained identifies the second temperature as the most significant influencing factor in producing MBT by this route. The initial temperature, $T_1$, (150° C.) does not impact the formation of MBT as significantly as the final temperature, $T_2$, (235° C.). The estimated yields from the regression indicate that the maximum MBT would be produced at the shortest time at $T_1$ and the longest at $T_2$. When $T_2$ equals 3 hours, the yield is approximately the same if $T_1$ were held for 1 or 2 hours, indicating the importance of $T_2$ on the yield of MBT.

Spread sheet quadratic regression provides estimated yields that indicate that $T_2$ held for the maximum of three hours produces the highest yield of MBT. Further, the spread sheet regression indicates that the reaction should be held at $T_1$ for approximately two hours.

In view of the many changes and modifications that can be made without departing from principles underlying the invention, reference should be made to the appended claims for an understanding of the scope of the protection to be afforded the invention.

What is claimed is:

1. In a process for the preparation of 2-mercaptobenzothiazole by reacting aniline, nitrobenzene, and carbon disulfide, the improvement comprising employing a reaction temperature profile comprising the steps of:

(A) heating the reactants to at least one temperature in the range of from about 140° C. to about 150° C. for at least one hour;

(B) then heating the reactants to a temperature in the range of from about 150° C. to about 170° C.; and (C) then heating the reactants to a temperature in the range of from about 220° C. to about 275° C.

2. The process of claim 1 wherein the carbon disulfide is employed in a molar excess.

3. The process of claim 2 wherein the molar excess is about fifty percent.

4. The process of claim 2 wherein the molar excess is about sixteen percent.

5. The process of claim 1 wherein step (A) is run for two hours, step (B) is run for one hour, and step (C) is run for three hours.

6. The process of claim 1 wherein step (A) is run for one hour, step (B) is run for one hour, and step (C) is run for two hours.

7. The process of claim 1 wherein step (A) is run for two hours, step (B) is run for one hour, and step (C) is run for two hours.

8. The process of claim 1 wherein steps (A) and (B) are both run at about 150° C.

9. The process of claim 8 wherein steps (A) and (B) are run for a total of one to two hours and step (C) is run for three hours.

* * * * *